(12) United States Patent
Kiyuna

(10) Patent No.: US 8,571,279 B2
(45) Date of Patent: Oct. 29, 2013

(54) SPOT QUANTIFICATION APPARATUS, SPOT QUANTIFICATION METHOD, AND RECORDING MEDIUM

(75) Inventor: Tomoharu Kiyuna, Tokyo (JP)

(73) Assignee: NEC Corporation, Tokyo (JP)

( * ) Notice: Subject to any disclaimer, the term of this patent is extended or adjusted under 35 U.S.C. 154(b) by 676 days.

(21) Appl. No.: 12/354,629

(22) Filed: Jan. 15, 2009

(65) Prior Publication Data

US 2010/0021028 A1 Jan. 28, 2010

(30) Foreign Application Priority Data

Jan. 18, 2008 (JP) ................................ 2008-009261

(51) Int. Cl.
*G06K 9/00* (2006.01)

(52) U.S. Cl.
USPC ............ 382/128; 382/190; 382/133; 382/205

(58) Field of Classification Search
USPC .................. 382/190, 128, 133, 205; 356/496
See application file for complete search history.

(56) References Cited

U.S. PATENT DOCUMENTS

2005/0169517 A1* 8/2005 Kasai ............................ 382/159

FOREIGN PATENT DOCUMENTS

| JP | 06-259784 A | 9/1994 |
|---|---|---|
| JP | 2003-303344 A | 10/2003 |
| JP | 2004-101354 A | 4/2004 |
| JP | 2004-535569 A | 11/2004 |
| JP | 2006-505782 A | 2/2006 |
| JP | 2006-084281 A | 3/2006 |

OTHER PUBLICATIONS

Thomann et al: "Automatic fluorescent tag detection in 3D with super-resolution: application to the analysis of chromosome movement", Journal of Microscopy, vol. 208, Pt 1 Oct. 2002, pp. 49-64.*
Muto et al: JP2006-084281—English-version, which was translated by machine.*
Thomann D, Danuser G, "Automatic fluorescent tag detection in 3D with super-resolution: Application to the analysis of chromosome movement", Journal of Microscopy, Oct. 2012, vol. 208, No. 1, pp. 49-64, Cited in Japanese Office Action.
Japanese Office Action for JP2008-009261 mailed on May 7, 2013 with English Translation.
Japanese Office Action for JP 2008-009261 mailed on Apr. 9, 2013 with English Translation.

* cited by examiner

*Primary Examiner* — Ruiping Li

(57) ABSTRACT

A spot quantification apparatus includes an image input unit, a filtering unit, and a spot quantification unit. The image input unit receives an image including a spot. The filtering unit filters the image input through the image input unit a plurality of times while changing a parameter of a kernel within a predetermined range. The spot quantification unit quantifies a feature of the spot based on the luminance distribution in each image which has been filtered a plurality of times by the filtering unit.

10 Claims, 11 Drawing Sheets

Fig.8

| RADIUS OF INTERNAL CIRCLE | PEAK VALUE (P6) | PEAK VALUE (P7) |
|---|---|---|
| 0.04 | 0.13 | 1.22 |
| 0.06 | 0.24 | 1.72 |
| 0.08 | 0.35 | 1.70 |
| 0.10 | 0.47 | 1.51 |
| 0.12 | 0.59 | 1.31 |
| 0.14 | 0.66 | 1.13 |
| 0.16 | 0.71 | 0.98 |
| 0.18 | 0.70 | 0.88 |
| 0.20 | 0.68 | 0.79 |

SPOT QUANTIFICATION APPARATUS, SPOT QUANTIFICATION METHOD, AND RECORDING MEDIUM

This application is based upon and claims the benefit of priority from Japanese Patent Application No. 2008-009261 filed on Jan. 18, 2008, the content of which is incorporated by reference.

BACKGROUND OF THE INVENTION

1. Field of the Invention

The present invention relates to technologies for quantifying features of spots included in an image.

More particularly, the present invention relates to technologies for quantifying features of spots in an image which includes a plurality of spots that correspond to genes or chromosomes labeled by fluorescent antibodies.

2. Description of the Related Art

In the medial field based on biotechnology, genes or chromosomes are labeled by fluorescent antibodies, and their aspects are observed in order to diagnose a variety of diseases represented by cancer.

Specifically, when genes or chromosomes labeled by fluorescent antibodies are observed with a microscope, the resulting image includes fluorescent regions (hereinafter referred to as "spots") which correspond to these genes or the like. This image is digitized and captured into a computer which only detects spots corresponding to genes or chromosomes subjected to diagnosis, and quantitatively analyzes features of the detected spots, such as the size, shape and the like of the spots. Then, a doctor diagnoses diseases based on the quantified features of the spots.

For example, in a diagnosis of chronic myeloid leukemia, an important diagnostic index lies in the presence or absence of dislocation between carcinogenic gene c-abl on a ninth chromosome and a bcr gene on a 22-th chromosome. Accordingly, the presence or absence of dislocation is determined on the basis of a feature amount of spots corresponding to these genes, and a doctor makes a diagnosis.

While a laboratory technician can visually observe an image to detect spots corresponding to chromosomes subjected to diagnosis and quantify their features, this method is likely to depend on the laboratory technician's personal point of view and therefore implies problems in objectivity, reproductivity, and quantitativity. Thus, attempts have been made in diagnoses of diseases to automatically quantify features of spots in an objective manner on a computer.

A computer-based apparatus or method of quantifying features of spots involves finding a point at which the intensity (luminance) of a spot reaches a peak, setting n line segments centered at the peak point, finding n points at which the luminance presents predetermined value (th) for a luminance distribution of each line segment, minimal-elliptic-approximating an n-gon formed by connecting these points, and measuring the spot diameter, as disclosed in JP-H6-259784-A (Patent Document 1).

Also, as disclosed in JP-2004-535569-A (Patent Document 2), there is an apparatus or method which divides a region representative of a cell nucleus from the remaining region, and quantitatively analyzes a spot shape based on a luminance distribution of the divided region.

Here, when noise occurs, a computer reduces the noise by filtering with the use of a predetermined kernel in order to correctly perform a quantitative analysis, as disclosed in JP-2006-505782-A (Patent Document 3). Alternatively, as disclosed in JP-2006-084261-A (Patent Document 4), a computer sets a variable spot recognition region for recognizing one spot, and detects a spot based on a change in signal strength distribution when the size of the spot recognition region is changed, thereby suppressing the influence of noise.

However, the technologies described above have problems as shown below.

The apparatus or method disclosed in Patent Document 1 must perform a procedure for finding n points, and a procedure for minimal-elliptic-approximating an n-gon, in addition to a procedure for finding the peak of a luminance distribution, and a procedure for measuring features becomes complicated. Then, the method disclosed in Patent Document 3 must previously obtain a large number of experiment data for patterns of parameters contained in a region which represents a cell nucleus, and is therefore not a convenient method.

Also, the apparatus or method disclosed in Patent Document 3 or 4 fails to sufficiently suppress the influence of noise, and has a problem in which the quantitative analysis on features of spots is made incorrect due to noise and varying luminance.

SUMMARY OF THE INVENTION

It is an exemplary object of the present invention to provide a technology which is capable of quantifying a feature of a detected spot in a simple and correct manner.

To achieve the above object, an exemplary aspect of the invention is a spot quantification apparatus which comprises image input means for inputting an image including a spot, filtering means for filtering the image input through the image input means a plurality of times while changing a parameter of a kernel within a predetermined range, and spot quantifying means for quantifying a feature of the spot based on a luminance distribution in each image which has been filtered a plurality of times by the filtering means.

A spot quantification method according to the present invention includes inputting an image including a spot, filtering the input image a plurality of times while changing a parameter of a kernel within a predetermined range, and quantifying a feature of the spot based on a luminance distribution in each image which has been filtered a plurality of times.

A program according to the present invention causes a computer to implement a function that includes performing a filtering procedure that is configured to filter an image including a spot a plurality of times while changing a parameter of a kernel within a predetermined range, and a spot quantification procedure that is configured to quantify a feature of the spot based on a luminance distribution in each image region which has been filtered a plurality of times by the filtering procedure.

The above and other objects, features, and advantages of the present invention will become apparent from the following description with references to the accompanying drawings which illustrate examples of the present invention.

BRIEF DESCRIPTION OF THE DRAWINGS

FIG. 8 is a diagram showing an example of a feature amount resulting from filtering using concentric kernels in the first exemplary embodiment;

DETAILED DESCRIPTION OF THE PREFERRED EMBODIMENTS

First Exemplary Embodiment

A first exemplary embodiment for implementing the present invention will be described in detail with reference to FIGS. 1 to 9.

Figure 1:
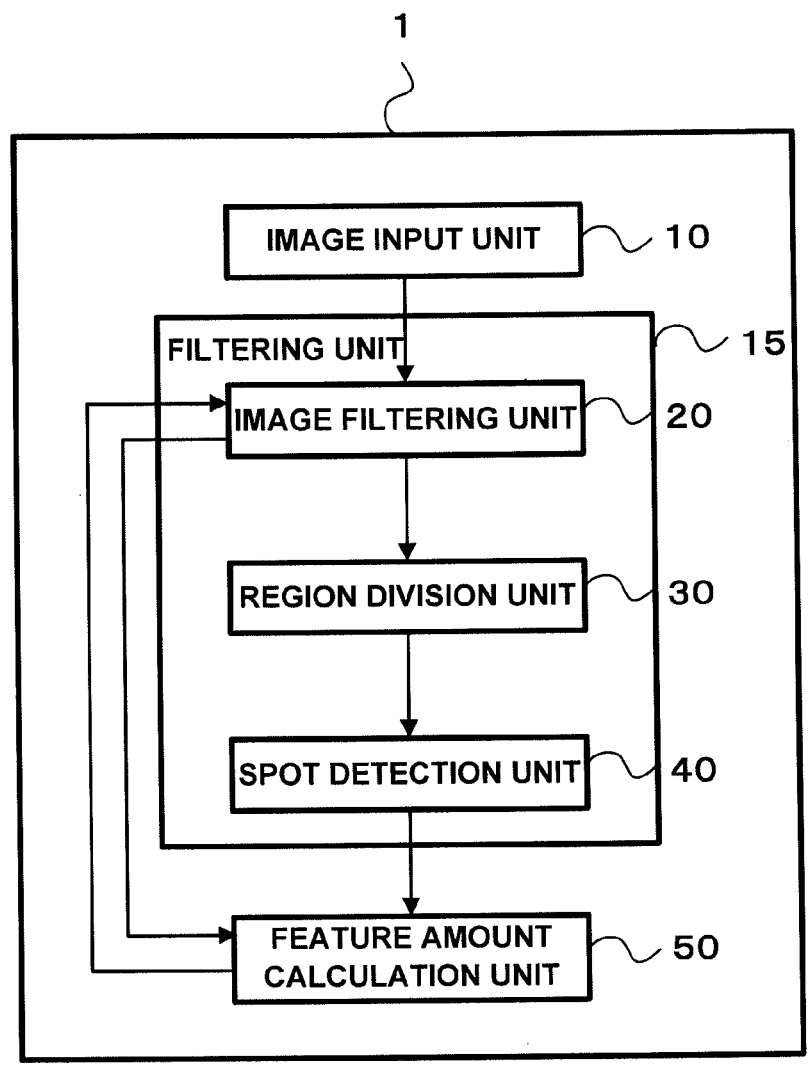
FIG. 1 is a block diagram showing the configuration of a spot quantification apparatus according to a first exemplary embodiment.

FIG. 1 is a block diagram showing the configuration of spot quantification apparatus 1 of this exemplary embodiment. Referring to FIG. 1, spot quantification apparatus 1 comprises image input unit 10, filtering unit 15, and feature amount calculation unit 50.

An image which includes spots corresponding to fluorescently dyed genes or chromosomes is inputted into spot quantification apparatus 1 through image input unit 10.

Figure 2:
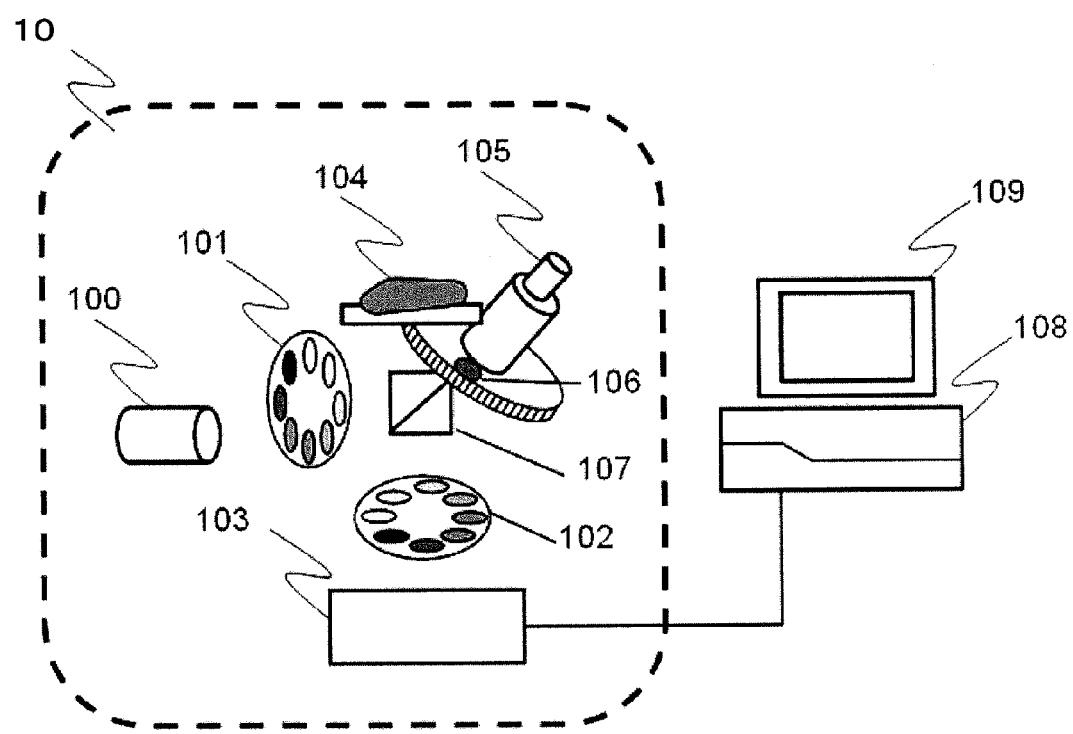
FIG. 2 is a diagram showing an exemplary configuration of the spot quantification apparatus in the first exemplary embodiment.

This image input unit 10 comprises, for example, light source 100, excitation filter 101, barrier filter 102, CCD camera 103, sample 104, eyepiece 105, objective lens 106, and dichroic mirror 107, as shown in FIG. 2.

The user observes an image of sample 104 through eyepiece 105 and objective lens 106, and selects excitation filter 101 and barrier filter 102 which are compatible with the waveform characteristic of a fluorescent reagent.

Then, sample 104 is irradiated with excited light from light source 100, reflected by dichroic mirror 107 through selected excitation filter 101. The image of this sample 104 is passed through dichroic mirror 107 and barrier filter 102, which separate light in a predetermined wavelength range, and is captured by CCD camera 103.

Turning back to FIG. 1, image filtering unit 15 filters image data input through image input unit 10. This filtering unit 15 comprises image filtering unit 20, region division unit 30, and spot detection unit 40.

Image filtering unit 20 filters image data input through image input unit 10 using a kernel (mask) defined by a predetermined parameter. Image filtering unit 20 produces a filtered image by convolusionally integrating a filter function which defines the kernel and the input image in the filtering.

Image filtering unit 20 can employ, for example, a Gaussian kernel defined by the following Equation (1) or (2) as the kernel:

$$K(x) = \frac{1}{2\pi h^2} \exp(-x^2/h^2) \tag{1}$$

where $K(x)$ is a filter function, $x$ is an input value for luminance, and $h$ is a band width.

$$K(x, y) = \frac{1}{2\pi\sqrt{1-\rho^2}} \exp\left[-\frac{1}{2(1-\rho^2)}\{(x/h_1)^2 - 2\rho(x/h_1)(y/h_2) + (y/h_2)^2\}\right] \tag{2}$$

where $K(x,y)$ is a filter function, $x$ is an input value for luminance, $h_1$ is a band width in the x-axis direction, $h_2$ is a band width in the y-axis direction, and ※ is a parameter for determining the direction of the axis.

Alternatively, image filtering unit 20 can also use an Epanechnikov kernel defined by the following Equation (3) as the kernel:

$$K(x) = \frac{2}{\pi}[1 - (|x|/h)^2]I_{\{|x|\leq h\}} \tag{3}$$

where $K(x)$ is a filter function, $x$ is an input value for luminance, $|x|$ is the absolute value of an input vector, and $h$ is a band width. Ic is an indicator function which takes a value of one when condition C is established and otherwise takes a value of zero.

Alternatively, image filtering function 20 can also uses a concentric kernel defined by the following Equation (4) as the kernel:

$$K(x) = \frac{1}{\pi r_1^2} I_{\{|x|\leq r_1\}} - \frac{1}{\pi(r_2^2 - r_1^2)} I_{\{r_1 < |x|\leq r_2\}} \tag{4}$$

where $K(x)$ is a filter function, $x$ is an input value for luminance, $|x|$ is the absolute value of an input vector, $r_1$ is the radius of an internally concentric circle, and $r_2$ is the radius of an external concentric circle.

Alternatively, image filtering unit 20 can also uses a Mexican hat kernel defined by the following Equation (5) as the kernel:

$$K(x) - 1 - (|x|/h)^2]\exp[-(|x|/h)^2] \tag{5}$$

where $K(x)$ is a filter function, $x$ is an input value for luminance, $|x|$ is the absolute value of an input vector, and $h$ is a band width.

Next, region division unit 30 divides the image filtered by image filtering unit 20 into image regions which include spots and image regions which include no spot based on the distance between the centers of the spots. A procedure for dividing the image into image regions will be described later in greater detail.

Spot detection unit 40 finds a luminance distribution within each image region for the image regions, divided by region division unit 30, which include spots, and detects its peak spot as the center position of the spot (hereinafter referred to as the "spot position"). Also, spot detection unit 40 transmits the original image, before image filter unit 20 has filtered the image, to feature amount calculation unit 50.

Feature amount calculation unit 50 extracts a rectangular area of a predetermined size centered at the position of the spot detected by spot detection unit 40 from the original image before it is filtered. Then, feature amount calculation unit 50 filters the extracted rectangular area using a kernel defined by different parameters to calculate a feature amount of the spot. As the kernel which is to be used, any of the aforementioned kernel, for example, is selected. A method of quantifying the feature amount of the spot will be described later.

Features of the spot quantified by feature amount calculation unit 50 includes the size, area, boundary length, shape and the like of the spot. The quantified shape includes the ratio of a longer axis to a shorter axis, the angle formed by the longer axis and shorter axis, circularity and the like.

The circularity of the spot is calculated, for example, according to the following Equation (6):

$$2\sqrt{\pi S}/L \qquad (6)$$

where S is the area of the spot, and L is the length of the boundary of the spot. The circularity takes a value of one when the spot is a true circle in shape and otherwise takes a value smaller than one.

The aforementioned image filtering unit 20, region division unit 30, spot detection unit 40, and feature amount calculation unit 50 are configured, for example by computer 108 such as a personal computer and monitor 109 such as a liquid crystal display device, as shown in FIG. 2.

Next, the operation of spot quantification apparatus 1 will be described in detail with reference to FIGS. 3 and 4.

Figure 3:
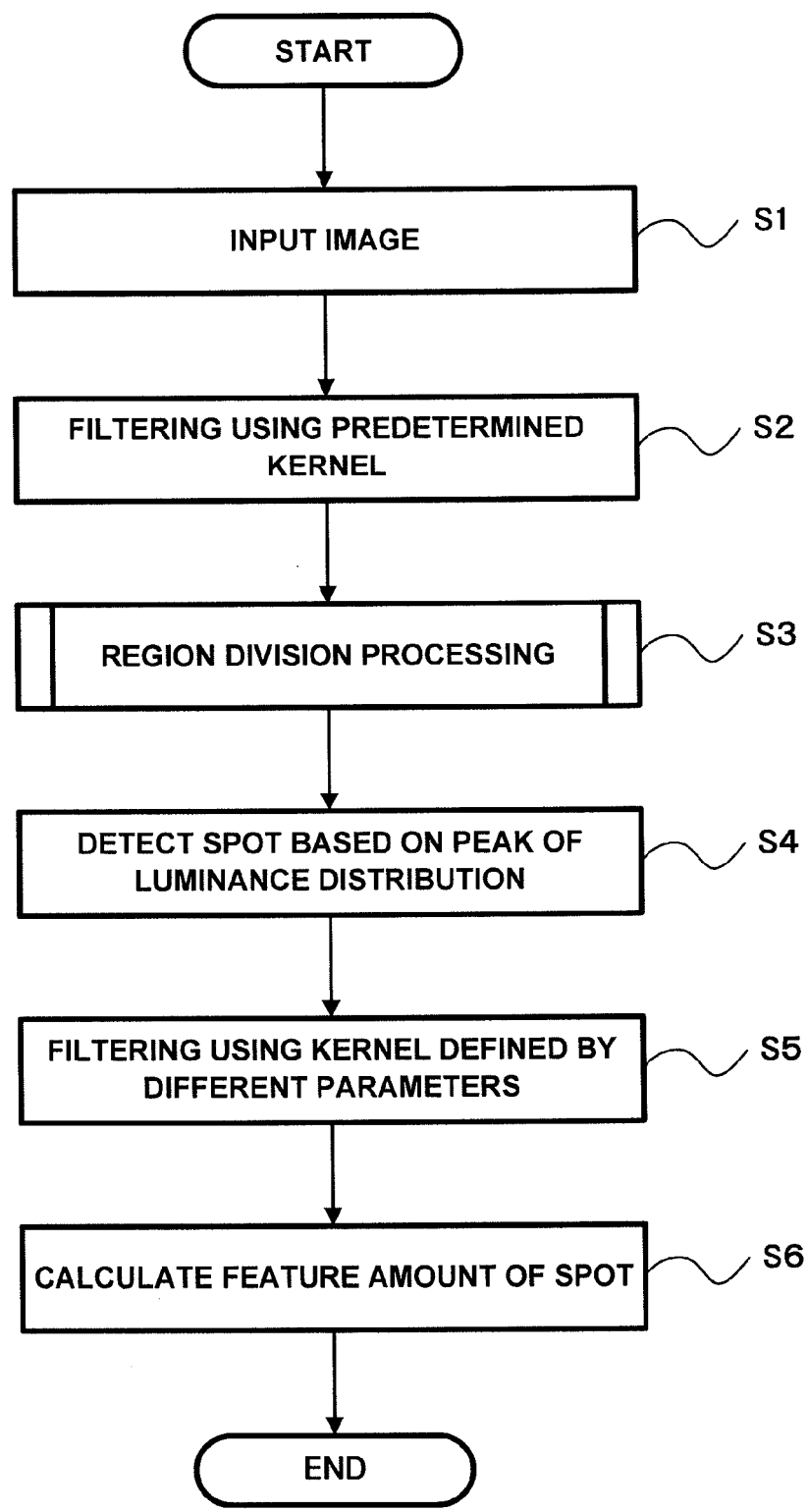
FIG. 3 is a flow chart showing a processing procedure of a spot quantification method in the first exemplary embodiment.

FIG. 3 is a flow chart showing the processing procedure of a spot quantification method in the first exemplary embodiment.

First, spot quantification apparatus 1 is applied with an image including spots corresponding to genes or chromosomes through image input unit 10 (step S1).

Image filtering unit 20 filters the input image using a predetermined kernel defined by the aforementioned Equation (1)-(5) or the like (step S2).

Region division unit 30 divides the filtered image into image regions which include spots and image regions which include no spots (step S3).

The region division processing executed at step S3 will be described in detail with reference to FIG. 4. FIG. 4 is a flow chart showing the processing procedure of the region division method.

Figure 4:
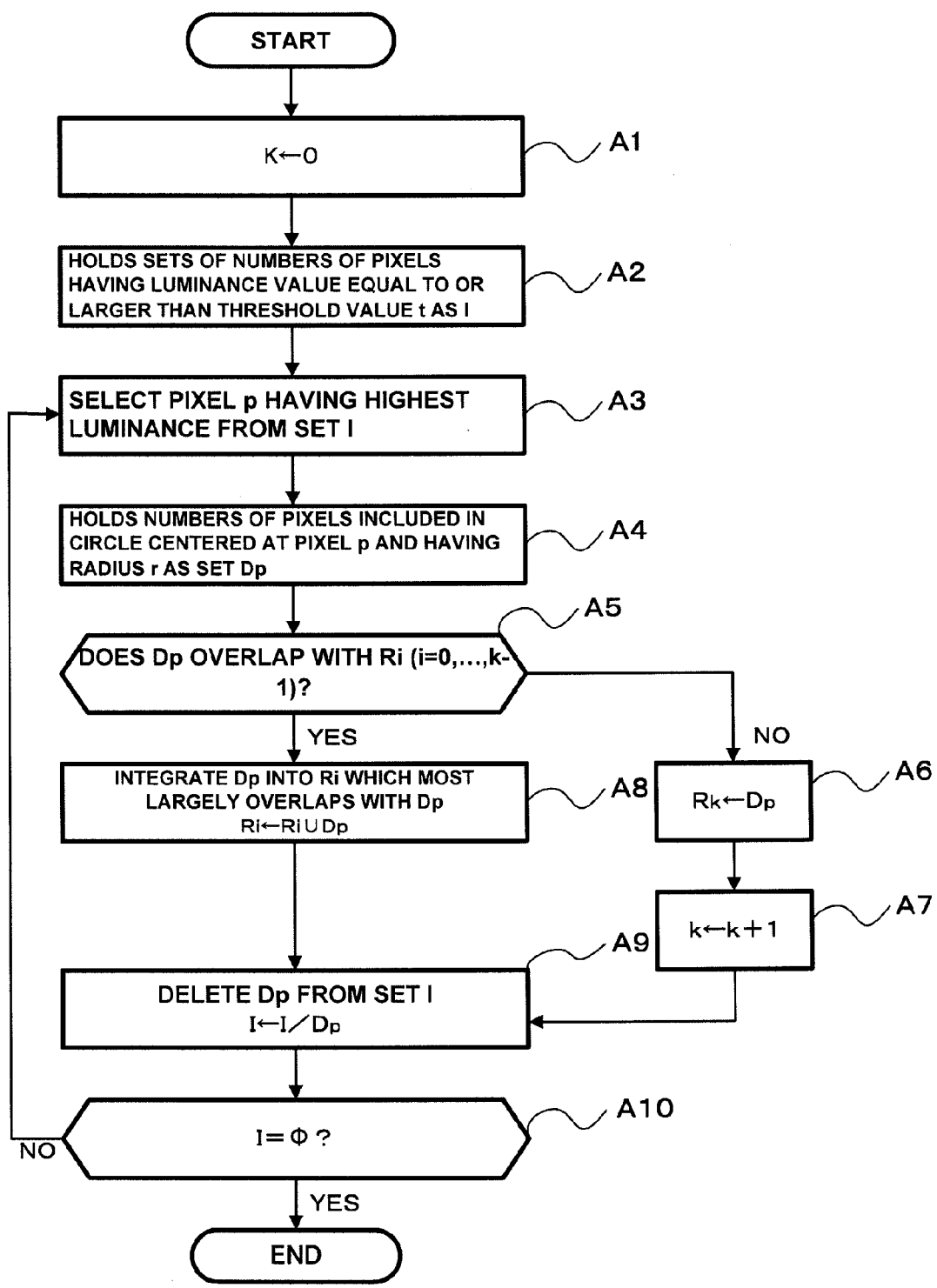
FIG. 4 is a flow chart showing a processing procedure of a region division method in the first exemplary embodiment.

Referring to FIG. 4, region division unit 30 first initializes an initial value for region number k to zero (step A1). This region number k is an integer which is assigned to each image region which is divided as a region including spots in the region division processing (step S3).

Region division unit 30 gets a luminance distribution of the input image. Then, region division unit 30 holds pixel numbers of pixels in the input image which have a luminance value equal to or larger than predetermined threshold value t as set I (step A2). Threshold t used herein may be a value sufficiently small as compared with the average luminance of the input image, and may be set to zero in some cases to include pixel numbers of all pixels in set I. Set I refers to a set of pixel numbers of pixels within an image region which is subjected to a search for a spot in the input image. Also, as the pixel number, for example, a value indicative of the coordinate of a pixel is used.

Region division unit 30 selects pixel p which has the highest luminance from pixels included in set I (step A3).

Region division unit 30 finds pixel numbers of all pixels included in a circle centered at pixel p selected at step A3 and having a predetermined radius r, and holds them as set $D_p$ (hereinafter referred to as "neighborhood set") (step A4). The value of this radius r may be a value sufficiently larger than the size of a spot subjected to detection.

Region division unit 30 determines whether or not set $R_i$ (i=0, . . . , k−1) overlaps with neighborhood set $D_p$ (step A5). Here, $R_i$ (i=0, . . . , k−1) refers to a set of pixel numbers of pixels within the image region extracted by region division processing, and $R_i$ has not yet been found when step A5 is executed for the first time (when k=0).

When $R_i$ does not overlap with $D_p$, or when $R_i$ has not been found (NO at step A5), region division unit 30 designates neighborhood set $D_p$ as set $R_k$ (step A6). Then, region division unit 30 increments the value of region number k by one (step A7).

When $R_i$ overlaps with $D_p$ (YES at step A5), region division unit 30 finds the number of elements in a common set between neighborhood set $D_p$ and $R_i$ as the size of the overlapping, and integrates $D_p$ into $R_i$ which maximizes the size of the overlapping (step A8). When there are a plurality of $R_i$ which maximize the size of the overlapping, $R_i$ which should be integrated is selected, for example, by a method of finding $R_i$ which has the smallest region number, finding $R_i$ which has the largest region size, or the like.

After step A7 or A8, region division unit 30 deletes neighborhood set $D_p$ for which the search has been completed from set I (step A9).

Region division unit 30 determines whether or not set I includes unsearched pixels, i.e., whether or not set I is an empty set (I=ϕ) (step A10).

When set I is an empty set (YES at step A10), region division unit 30 terminates the region division processing because all regions have been searched, and spot detection unit 40 executes step S4. When set I is not an empty set (NO at step A10), region division unit 30 returns to step A3.

In this way, in region division processing (steps A1-A10), region division unit 30 integrates neighboring regions of peaks which are closely spaced from each other by a predetermined distance or less, among a plurality of peaks, into a single image region. Generally, when a plurality of peaks exist, peaks closely spaced from each other and having relatively low intensities are often secondary peaks with respect to peaks having relatively high intensities or noise. Accordingly, by detecting a peak having the highest luminance in each integrated image region, it is possible to remove secondary peaks and noise within that region.

Also, in the region division processing, region division unit 30 groups peaks which are spaced from each other by a predetermined distance or more into different image regions. Generally, when there are a plurality of peaks, a peak spaced from a certain referred peak by the predetermined distance is often a peak corresponding to a different independent spot, rather than noise or secondary peak. Accordingly, by detecting a spot in each extracted region, it is possible to detect even a peak that has a signal with a relatively low intensity as a spot.

Turning back to FIG. 3, spot detection unit 40 detects a peak point of a luminance distribution in each extracted image region, and performs a procedure for detecting a spot with this peak point being regarded as the position of the spot (step S4).

Feature amount calculation unit 50 extracts a predetermined rectangular area centered at the detected position of the spot from the original image before filtering, and filters this rectangular area using a kernel with varied parameters (step S5).

Here, feature amount calculation unit 50 predicts a parameter value which is consistent with a feature amount of a spot to be detected, and varies the parameter within a predetermined range before and after the predicted value. For example, with a Gaussian kernel, feature amount calculation unit 50 assumes that a spot to be detected has a size (for example, the radius) of R, and varies a parameter (for example, a band width) of the kernel from h (band width) =0.5R to h=2R in increments of 0.1 for filtering the rectangular area.

Then, feature amount calculation unit 50 calculates a feature amount of the spot in the rectangular area (step S6). After step S6, spot quantification apparatus 1 terminates spot quantification processing.

A specific method of calculating a feature amount will be described. At step 5, spot quantification apparatus 1 normalizes a luminance distribution within a rectangular area extracted from the original image, for example, such that the sum of luminance within the rectangular area is equals to one. This normalized rectangular area is filtered in the aforementioned manner to find the peak value of the luminance distribution after the filtering.

Spot quantification apparatus 1 repeatedly performs the filtering and peak value search using a kernel defined by different parameters (for example, a band width).

Generally, the luminance distribution of a spot often has a shape in which the luminance slowly changes from the center position toward the peripheries. Even if a method of only extracting pixels that have a luminance value equal to or larger than a predetermined threshold value is simply applied to an image which includes a spot having this luminance distribution, the shape of the spot cannot be correctly detected. Thus, by performing filtering using a filter function which gradually changing the weighting from the center position toward the peripheries, for example, as represented by Equations (1)-(5), the shape of the spot can be correctly detected. Spot quantification apparatus 1 performs filtering a plurality of times while changing parameters (for example, a band width) of the filter function to find a parameter which enables a spot to be most clearly detected. Since the waveform of a filter function corresponding to this optimal parameter is highly consistent with the shape of an actually fluorescently processed gene or the like (spot), the shape of a spot to be detected can be correctly found from the optimal parameter value.

For example, when a Gaussian kernel (Equation (1)) is used, in a series of peak values detected a plurality of times, band width h which defines the kernel at the time that a maximum peak value is detected substantially matches with the diameter of the spot.

When a Gaussian kernel is used as defined by Equation (2), spot quantification apparatus 1 can find the ratio of the longer axis to the shorter axis, the area of the spot, the angle formed by the longer axis and shorter axis and the like from band widths $(h_1, h_2)$ on the x-axis, y-axis corresponding to the maximum peak value. And the spot quantification apparatus 1 can find parameter $\rho$ from parameter $\sigma$ which determines the directions of the axes, Likewise, when a kernel is used as defined by Equation (3) or Equation (5), band width h corresponds to the diameter of the spot. When a kernel is used as defined by Equation (4), radius $r_1$ of the internal circle substantially matches the diameter of the spot.

In this way, at step 6, spot quantification apparatus 1 can quantify a feature of the spot in a simple procedure by finding a parameter corresponds to the maximum peak value.

Next, exemplary results of the spot quantification processing executed in accordance with the first exemplary embodiment are shown in FIGS. 5-9.

Figure 5:
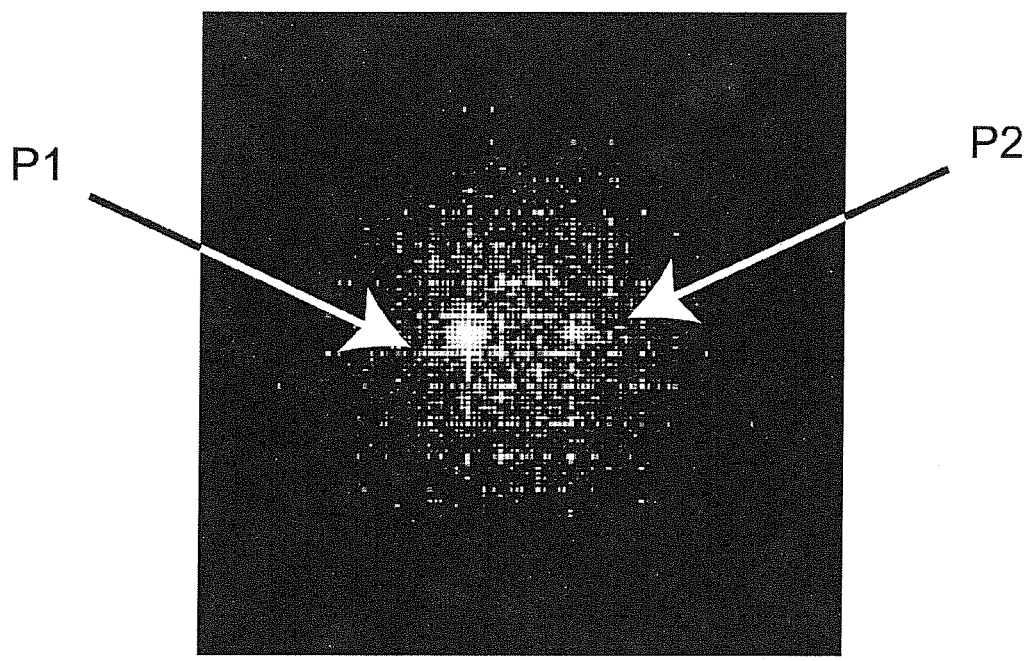
FIG. 5 is a diagram showing an example of an input image in the first exemplary embodiment.

FIG. 5 is an example of an original image, before filtering, input to spot quantification apparatus 1. As shown in FIG. 5, this image includes one or a plurality of spots corresponding to fluorescently dyed genes or chromosomes.

Figure 6:
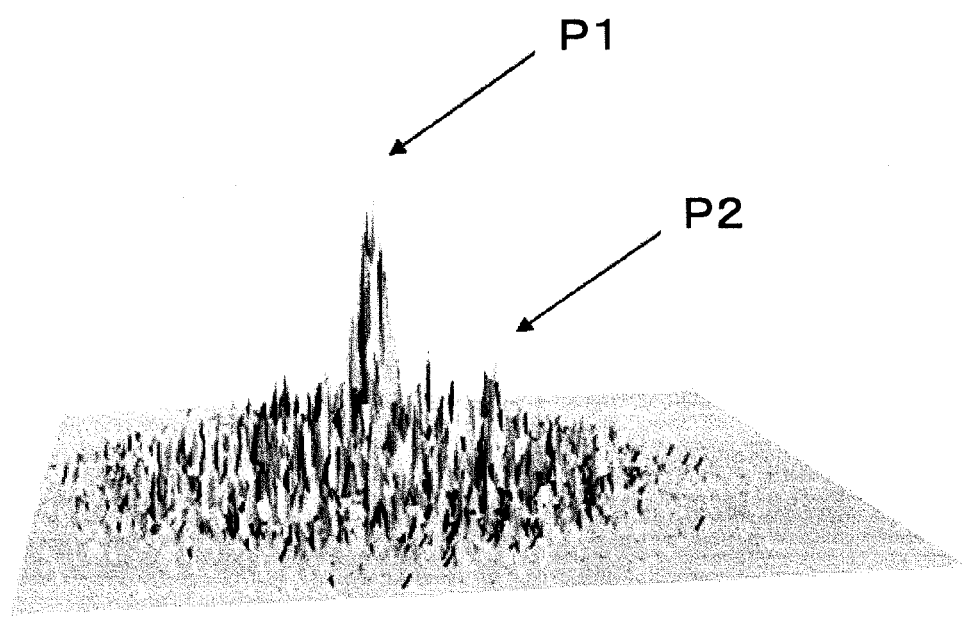
FIG. 6 is a diagram showing an example of a luminance distribution of an input image in three-dimensional representation in the first exemplary embodiment.

FIG. 6 is a diagram which shows the signal intensity (luminance) in the image shown in FIG. 5 in three-dimensional representation. Referring to FIGS. 5 and 6, the input image includes spot P1 of a relatively strong signal, and spot P2 of a relatively weak signal. Then, noise is introduced around spot P1. Since this noise can cause to fail to capture the spot or to erroneously detect a false spot, an attempt is made to reduce the noise.

For reducing noise, spot quantification apparatus 1 detects a peak equal to or larger than a predetermined threshold value as a spot when it detects a spot, for example, based on a luminance distribution of the image. However, since the intensity of the noise can be larger than the signal intensity of a spot to be detected, a problem arises in that a weak signal is more likely to be missed if the threshold value is increased to avoid the noise, but noise can be picked up to result in erroneous detection of a false spot if the threshold value is reduced on the contrary in order to pick up a week signal. This problem can be overcome by performing the filtering (step S2) shown in FIG. 3 and the region division processing (step A1-A10) shown in FIG. 4.

Figure 7:
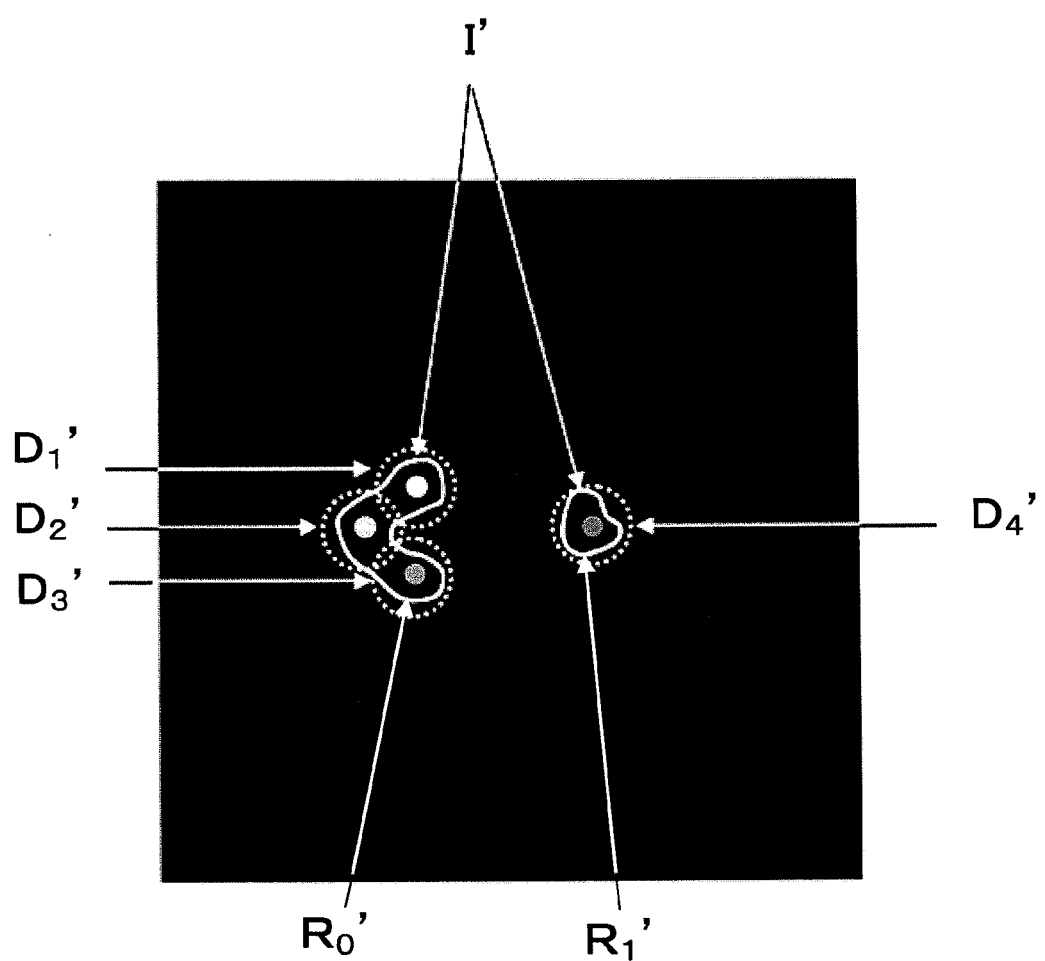
FIG. 7 is a diagram showing an example of image regions divided by region division processing in the first exemplary embodiment.

FIG. 7 shows an image after the region division processing. Region I' surrounded by a white solid line, shown in FIG. 7, represents a region corresponding to set I of pixel numbers of pixels which have a luminance equal to or larger than predetermined threshold t (step A2). Regions $D_i'$ (i=1, 2, 3, 4) within a circle surrounded by a white dotted line represent regions corresponding to neighborhood sets Di which include a pixel number of a pixel, the luminance of which is i-th higher, respectively.

In the region division processing described above, first, neighborhood set $D_1$ is held, including a pixel number of a pixel within a circle having radius r, centered at a pixel having the highest luminance within set I (step A4). Since there is no $R_0$ in the first loop (NO at step A5), this $D_1$ is set to $R_0$ as it is (step A6). Next, $D_1$ is removed from set I (step A9), and neighborhood set $D_2$ is held, centered at a pixel having the highest luminance within the remaining set I (second highest luminance within enter set I) (step A6). Since $D_2$ overlap with previously extracted set $R_0$ (YES at step A5), $D_2$ is integrated into $R_0$, so that updated set $R_0$ results in $R_0 = D_1 \cup D_2$ (step A8). $D_2$ is further removed from set I (step A9), and neighborhood set $D_3$ is held, centered at a pixel having the highest luminance in the remaining set I (third highest luminance within enter set I) (step A6). Since $D_2$ also overlaps with $R_0$ (YES at step A5), $D_2$ is integrated into $R_0$, so that updated set $R_0$ results in $R_0 = D_1 \cup D_2 \cup D_3$ (step A8).

$D_3$ is further removed from set I (step A9), and neighborhood set $D_4$ is held, centered at a pixel having the highest luminance in the remaining set I (fourth highest luminance within enter set I) (step A6). Since this $D_4$ does not overlap with $R_0$ (NO at step A5), this $D_4$ is set to $R_1$ (step A6). When $D_4$ is removed from set I (step A9), set I becomes an empty set (YES at step A10), causing spot quantification apparatus 1 to terminate the region division processing.

Referring to FIG. 7, two image regions $R_0'$, $R_1'$ corresponding to sets $R_0$, $R_1$ have been extracted through the foregoing region division processing.

Then, spot detection unit 40 detects peak points of respective luminance distributions in extracted image regions $R_0'$, $R_1'$ as positions of spots (step S4).

By detecting spots in respective image regions $R_0'$, $R_1'$, it is possible to prevent erroneous detection of false spots within region $R_0'$ and reliably detect a spot of a weak signal within image region $R_1'$.

Subsequently, feature amount calculation unit 50 extracts predetermined rectangular areas centered at the detected positions of spots from the original image, and performs filtering several times using a kernel defined by different parameters to calculate feature amounts of the spots (step S6).

FIG. 8 shows the result of quantifying the features of the spots. Since two spots P6, P7 have been detected here, rectangular areas centered at the positions of these spots are filtered using a concentric kernel which has outer radius $r_1$ 1.5 times larger than inner radius $r_2$, with $r_2$ being changed from 0.04 to 0.2 in increments of 0.04. Referring to FIG. 8, in the area corresponding to spot P6, a maximum peak value of 1.72 is reached when the inner radius ($r_2$) is 0.16, while in the area corresponding to spot P7, a maximum peak value of 1.72 is reached when the inner radius ($r_2$) is 0.06. Since the inner diameter ($r_2$) substantially matches with the radius of the spot when the peak value of the spot reaches the maximum, the diameter of spot P6 is calculated to be approximately 0.32, and the diameter of spot P7 to be approximately 0.12 from these results. The values of these diameters are normalized by the size of the rectangular areas.

Whether or not the quantified feature amounts present correct values is confirmed by positively extracting the spots. FIGS. 9(a), 9(b) show examples of the luminance distributions of the spots detected at step S4 in one-dimensional representation. Referring to FIG. 9(a), spot P6 of a relatively large area has a diameter of approximately 0.3. And referring to FIG. 9(b), a diameter of spot P7, whose area is relatively small, is approximately 0.12.

Figure 9:
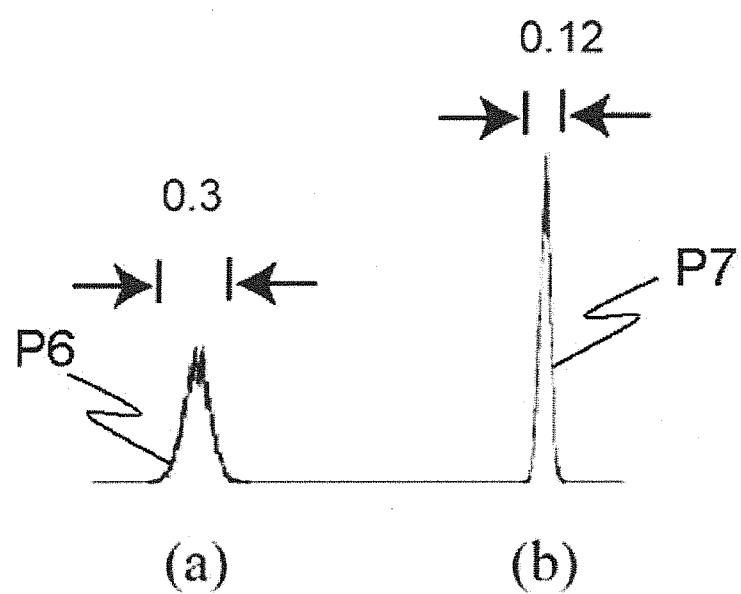
FIG. 9(a) is a diagram showing an example of a luminance distribution of a spot having a relatively large diameter in a one-dimensional representation in the first exemplary embodiment.
FIG. 9(b) is a diagram showing an example of a luminance distribution of a spot having a relatively small diameter in a one-dimensional representation in the first exemplary embodiment.

Accordingly, from the results of FIGS. 8(a), 8(b) and 9, it can be seen that the diameters of quantified spots fairly match with the diameters of the actual spots.

In this way, feature amount calculation unit 50 can simply and correctly quantify features of spots simply by performing filtering a plurality of times and examining the peak value of a luminance distribution in each image (step S6).

As described above, according to this exemplary embodiment, features of spots can be simply and correctly quantified because the features of the spots are quantified on the basis of luminance distributions in a plurality of images which have been filtered using a kernel while changing a parameter.

Also, according to this exemplary embodiment, spot quantification apparatus 1 filters an input image using a predetermined kernel, divides the filtered image into regions, detects spots positions in the divided image regions, and filters a predetermined image area centered at the detected position a plurality of times while a parameter of the kernel is changed in a predetermined range. It is therefore possible to further reduce noise in the filtering, and perform the quantification accurately even if there are changes in noise and luminance.

Second Exemplary Embodiment

A second exemplary embodiment for implementing the present invention will be described in detail with reference to FIGS. 10 and 11.

Figure 10:
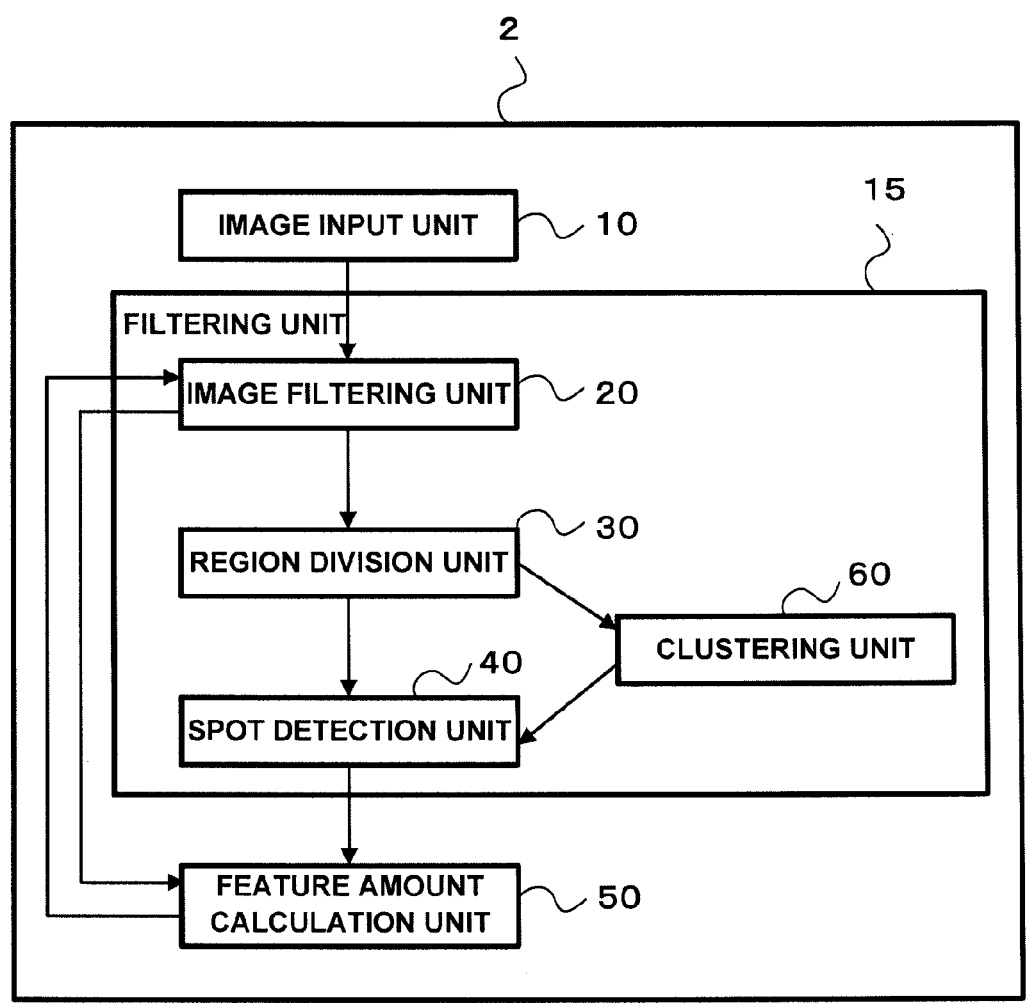
FIG. 10 is a block diagram showing the configuration of a spot quantification apparatus in a second exemplary embodiment.

FIG. 10 is a block diagram showing the configuration of spot quantification apparatus 2 of this exemplary embodiment. Referring to FIG. 10, spot quantification apparatus 2 is similar in configuration to spot quantification apparatus 1 except that filtering unit 15 comprises clustering unit 60.

Clustering unit 60 performs clustering for each pixel of an image region divided by region division unit 30 based on a luminance distribution, and extracts a region with relatively high luminance from this image region.

As shown in the second exemplary embodiment, even if a pixel having the highest luminance value is simply extracted within each of the image regions divided through the region division processing (step S4 in FIG. 3), secondary peaks and noise remaining in the region (for example peaks in regions $D_2'$, $D_3'$ in FIG. 7) are likely to be erroneously detected. Therefore, only a region having a relatively high average value of luminance (for example, region $D_1'$ in FIG. 7) is extracted through clustering, and spot detection unit 40 detects the peak value of the luminance distribution in the extracted region, thereby making it possible to avoid erroneous detection.

In the clustering, spot quantification apparatus 1 employs, for example, an image extraction method disclosed in JP-2003-303344-A which coarsely grains an image data space, and then repeats a calculation of a coarsely grained experience probability distribution, a calculation of a class attribution probability for each pixel, an update of parameters which define attributes of a class, and a calculation of an evaluation function, until the evaluation function no longer changes.

Next, the operation of spot quantification apparatus 1 will be described in detail with reference to FIG. 11.

Figure 11:
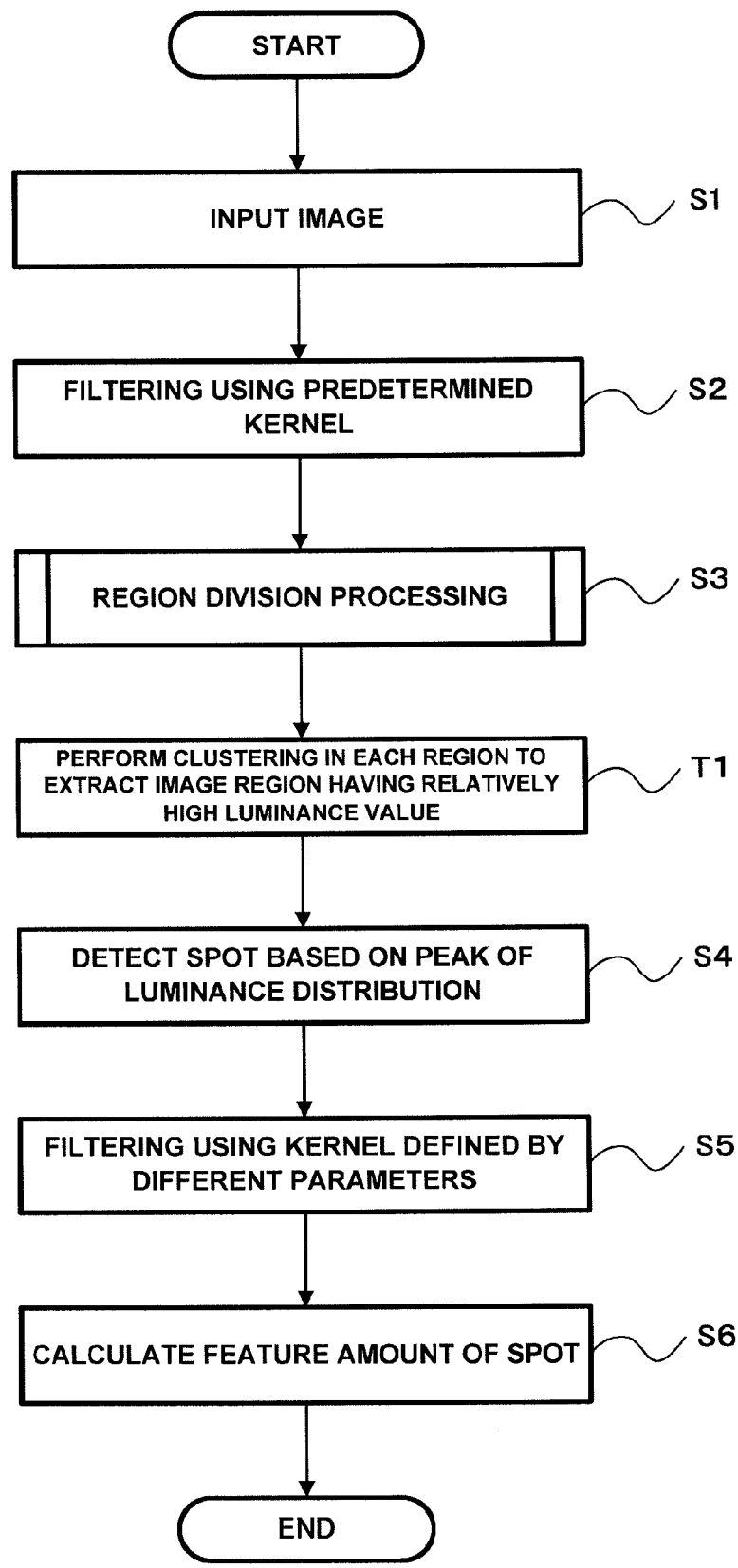
FIG. 11 is a flow chart showing a processing procedure of a spot quantification method in the second exemplary embodiment.

FIG. 11 is a flow chart showing the processing procedure of a spot quantification apparatus according to the second exemplary embodiment. Referring to FIG. 11, the spot quantification method of this exemplary embodiment is similar to the step quantification method according to the first exemplary embodiment except that step T1 is executed after step S3, and step S4 is executed after step T1.

After an image region has been extracted by region division processing (step S3), clustering unit 60 performs clustering for each pixel in the extracted image region to extract an image region which has a relatively high luminance value (step T1).

Then, spot detection unit 40 detects the peak spot of a luminance distribution for the image region extracted at step T1 as the position of a spot (step S4).

As described above, according to this exemplary embodiment, respective pixels in a divided image region are classified into a plurality of clusters based on a luminance distribution, and the position of a pixel having the highest luminance is detected as the position of a spot within pixels which belong to a cluster that presents the highest average value of luminance. It is therefore possible to further reduce noise which remains in image regions divided through image division processing and more correctly quantify the features of a spot.

The foregoing exemplary embodiment has been described in connection with an example in which a fluorescently dyed image of cells is input to quantify spots in gene regions labeled by a fluorescent antibody, but spot quantification apparatus 2 can analyze an image which is captured even by a different dying approach or capturing method, using the method according to this exemplary embodiment, as long as the image includes localized spots corresponding to chromosomes and the like within cell nucleuses and the image is represented by a luminance distribution.

In other cases where spot quantification apparatus 2 is even applied, for example, with a color image in which nucleuses and genes (or chromosomes) are captured on different channels of RGB (Red, Green, Blue), spot quantification apparatus 2 may break down the original image into three gray-scale images corresponding to RGB, and perform a similar procedure on the gray-scale images which include spots under analysis.

The kernel used in the filtering is not limited to those defined by the aforementioned Equations (1)-(5). Spot quantification apparatus 2 can use any other kernel than those described above provided that the kernel is suitable for reducing noise and quantifying features of spots.

When a parameter of a kernel is changed within a predetermined range to perform filtering a plurality of times (step S5 in FIG. 3), spot quantification apparatus 2 can employ a plurality of types of kernels, for example, a Gaussian kernel (Equation (1)), a Mexican hat kernel (equation (5)) and the like, rather than using only one of the kernels defined by Equations (1)-(5). In this event, spot quantification apparatus 2 changes a parameter in the respective kernel within a predetermined range to perform filtering, finds peak values of luminance, and quantifies the features of a spot based on the value of the parameter corresponding to the highest peak value of the found peak values.

Also, all or part of the processing at steps S2-S6 in FIG. 3 can be implemented by a computer program.

While preferred exemplary embodiments of the present invention have been described using specific terms, such description is for illustrative purposes only, and it is to be understood that changes and variations may be made without departing from the spirit or scope of the following claims.

What is claimed is:

1. A spot quantification apparatus comprising:
    an image input unit which receives an image including a spot;
    a filtering unit which filters the image input through said image input unit a plurality of times while changing a parameter of a kernel within a predetermined range; and
    a spot quantification unit which quantifies a feature of the spot based on a luminance distribution in each image which has been filtered a plurality of times by said filtering unit,
    wherein:
        said filtering unit changes a bandwidth of the kernel within a predetermined range to perform the filtering a plurality of times;
        said spot quantification unit finds peak values of a normalized luminance distribution in each image which has been filtered a plurality of times by said filtering unit, finds a maximum value in the peak values, and quantifies the bandwidth of the kernel used for an image in which the maximum value has been found;
        at least one of the image input unit, the filtering unit and the spot quantification unit is implemented by a processor;
        said kernel is a concentric kernel defined by:

$$K(x) = \frac{1}{\pi r_1^2} I_{\{|x| \leq r_1\}} - \frac{1}{\pi(r_2^2 - r_1^2)} I_{\{r_1 < |x| \leq r_2\}},$$

where K(x) is a filter function, x is an input value for luminance, $r_1$ is a radius of an internally concentric circle of the kernel, and $r_2$ is a radius of an external concentric circle of the kernel; and
said filtering unit changes a radius of an internal circle of the kernel within a predetermined range to perform the filtering a plurality of times.

2. A spot quantification apparatus comprising:
    image input means for inputting an image including a spot;
    filtering means for filtering the image input through said image input means a plurality of times while changing a parameter of a kernel within a predetermined range; and
    spot quantifying means for quantifying a feature of the spot based on a luminance distribution in each image which has been filtered a plurality of times by said filtering means,
    wherein:
        said filtering means changes a bandwidth of the kernel within a predetermined range to perform the filtering a plurality of times;
        said spot quantification means finds peak values of a normalized luminance distribution in each image which has been filtered a plurality of times by said filtering means, finds a maximum value in the peak values, and quantifies the bandwidth of the kernel used for an image in which the maximum value has been found;
        at least one of the image input means, the filtering means and the spot quantification means is implemented by a processor;
        said kernel is a concentric kernel defined by:

$$K(x) = \frac{1}{\pi r_1^2} I_{\{|x| \leq r_1\}} - \frac{1}{\pi(r_2^2 - r_1^2)} I_{\{r_1 < |x| \leq r_2\}},$$

where K(x) is a filter function, x is an input value for luminance, $r_1$ is a radius of an internally concentric circle of the kernel, and $r_2$ is a radius of an external concentric circle of the kernel; and
said filtering means changes a radius of an internal circle of the kernel within a predetermined range to perform the filtering a plurality of times.

3. The spot quantification apparatus according to claim 1, wherein said spot quantification unit quantifies the feature of the spot based on the values of the kernel used for an image in which the maximum value has been found.

4. The spot quantification apparatus according to claim 1, wherein said filtering unit changes the parameter of the kernel in a predetermined range including the value of the parameter that corresponds to the feature amount of the spot in order to perform the filtering.

5. The spot quantification apparatus according to claim 1, wherein said kernel is a Gaussian kernel.

6. The spot quantification apparatus according to claim 1, wherein said filtering unit comprises:
    a first filtering unit which filters an image input through said image input unit using a predetermined kernel;
    an image region division unit which divides the image filtered by said first filtering unit into an image region which includes spots and an image region which does not include spots based on the distance between the centers of spots;
    a spot detection unit which detects the center of a spot in the image region which includes spots, divided by said image region division unit, as the position of spot; and
    a second filtering unit which extracts a predetermined image area centered at the position of the spot detected by said image region division unit from the image input through said image input unit, and changes the parameter of the kernel within a predetermined range to filter the extracted image area a plurality of times.

7. The spot quantification apparatus according to claim 6, wherein said image region division unit groups spots which have their center points located within a predetermined distance from each other into the same image region, and groups spots which have their centers spaced from each other by the predetermined distance or more into different image regions, to divide the image filtered by said first filtering unit into an image region which includes the spots and an image region which does not include the spots.

8. The spot quantification apparatus according to claim 6, wherein said spot detection unit classifies respective pixels in the image region including spots, divided by said image region division unit, into a plurality of clusters based on a luminance distribution, and detects the position of a pixel having the highest luminance of pixels belonging to a cluster which presents the highest average value of luminance as position of spot.

9. A spot quantification method comprising:
inputting an image including a spot;
filtering the input image a plurality of times while changing a parameter of a kernel within a predetermined range; and
quantifying a feature of the spot based on a luminance distribution in each image which has been filtered a plurality of times,
wherein:
filtering further comprises changing a bandwidth of the kernel within a predetermined range to perform the filtering a plurality of times;
quantifying further comprises finding peak values of a normalized luminance distribution in each image which has been filtered a plurality of times, and quantifying the bandwidth of the kernel used for an image in which the maximum value has been found;
said kernel is a concentric kernel defined by:

$$K(x) = \frac{1}{\pi r_1^2} I_{\{|x| \leq r_1\}} - \frac{1}{\pi(r_2^2 - r_1^2)} I_{\{r_1 < |x| \leq r_2\}},$$

where $K(x)$ is a filter function, x is an input value for luminance, $r_1$ is a radius of an internally concentric circle of the kernel, and $r_2$ a radius of an external concentric circle of the kernel; and
filtering further comprises changing a radius of an internal circle of the kernel within a predetermined range to perform the filtering a plurality of times.

10. A non-transitory computer readable recording medium which has recorded thereon a program for causing a computer to perform these functions:
perform a filtering procedure configured to filter an image including a spot a plurality of times while changing a parameter of a kernel within a predetermined range; and
perform a spot quantification procedure configured to quantify a feature of the spot based on a luminance distribution in each image region which has been filtered a plurality of times by said filtering procedure,
wherein:
the filter procedure is further configured to change a bandwidth of the kernel within a predetermined range to perform the filtering a plurality of times;
the spot quantification procedure is further configured to find peak values of a normalized luminance distribution in each image which has been filtered a plurality of times, and quantify the bandwidth of the kernel used for an image in which the maximum value has been found;
said kernel is a concentric kernel defined by:

$$K(x) = \frac{1}{\pi r_1^2} I_{\{|x| \leq r_1\}} - \frac{1}{\pi(r_2^2 - r_1^2)} I_{\{r_1 < |x| \leq r_2\}},$$

where $K(x)$ is a filter function, x is an input value for luminance, $r_1$ is a radius of an internally concentric circle of the kernel, and $r_2$ is a radius of an external concentric circle of the kernel; and
the filter procedure is further configured to change the radius of an internal circle of the kernel within a predetermined range to perform the filtering a plurality of times.

* * * * *